US008034978B2

(12) United States Patent
Eberhardt et al.

(10) Patent No.: US 8,034,978 B2
(45) Date of Patent: Oct. 11, 2011

(54) PROCESS FOR THE PREPARATION OF AN AMINE

(75) Inventors: Jan Eberhardt, Mannheim (DE);
Harald Meißner, Haßloch (DE); Bram Willem Hoffer, Heidelberg (DE);
Johann-Peter Melder, Böhl-Iggelheim (DE); Ekkehard Schwab, Neustadt (DE)

(73) Assignee: BASF SE, Ludwigshafen (DE)

( * ) Notice: Subject to any disclaimer, the term of this patent is extended or adjusted under 35 U.S.C. 154(b) by 243 days.

(21) Appl. No.: 12/301,811

(22) PCT Filed: May 24, 2007

(86) PCT No.: PCT/EP2007/055054
§ 371 (c)(1),
(2), (4) Date: Nov. 21, 2008

(87) PCT Pub. No.: WO2007/137990
PCT Pub. Date: Dec. 6, 2007

(65) Prior Publication Data
US 2010/0267948 A1 Oct. 21, 2010

(30) Foreign Application Priority Data
May 31, 2006 (EP) ..................... 06114777

(51) Int. Cl.
C07C 209/26 (2006.01)
C07D 265/30 (2006.01)

(52) U.S. Cl. ........ 564/473; 564/446; 564/471; 564/472; 544/106

(58) Field of Classification Search .................. 564/397, 564/398, 446, 473
See application file for complete search history.

(56) References Cited

U.S. PATENT DOCUMENTS

| 3,275,554 A | | 9/1966 | Wagenaar | |
|---|---|---|---|---|
| 3,751,475 A | | 8/1973 | Van der Voport et al. | |
| 4,521,624 A | | 6/1985 | Jackisch | |
| 4,757,144 A | * | 7/1988 | Okabe et al. | 544/404 |
| 4,832,702 A | | 5/1989 | Kummer et al. | |
| 5,105,013 A | * | 4/1992 | Tanis et al. | 564/473 |
| 6,111,141 A | | 8/2000 | Eller et al. | |
| 6,884,887 B1 | | 4/2005 | Riermeier et al. | |
| 7,034,186 B2 | | 4/2006 | Gerlach et al. | |
| 7,230,134 B2 | | 6/2007 | Borner et al. | |
| 2005/0153846 A1 | | 7/2005 | Gatlin | |

FOREIGN PATENT DOCUMENTS

| CA | 1122981 A | 5/1982 |
|---|---|---|
| CN | 1092061 | 9/1994 |
| DE | 21 25 039 | 5/1970 |
| DE | 2118283 | 11/1972 |
| DE | 36 11 230 | 10/1987 |
| EP | 0007093 | 1/1980 |
| EP | 0312253 A2 | 4/1989 |
| EP | 0611137 A1 | 8/1994 |
| EP | 1020424 | 7/2000 |
| EP | 1202952 | 5/2002 |
| EP | 1 312 599 | 10/2002 |
| EP | 1 312 600 | 10/2002 |
| EP | 1431271 | 6/2004 |
| HU | 204764 | 8/1991 |
| JP | 2180854 | 7/1990 |
| JP | 2740828 | 7/1990 |
| JP | 2851274 | 3/1998 |
| JP | 10081650 | 3/1998 |
| JP | 2000-159731 | 6/2000 |
| WO | WO-03-014061 | 2/2003 |
| WO | WO-2007-107477 | 9/2007 |

OTHER PUBLICATIONS

International Preliminary Report on Patentability and Written Opinion issued in related International Application No. PCT/EP2007/055054 on Jan. 13, 2009.

* cited by examiner

Primary Examiner — Brian J Davis
(74) Attorney, Agent, or Firm — Connolly Bove Lodge & Hutz LLP

(57) ABSTRACT

Process for preparing an amine by reacting an aldehyde and/or ketone with hydrogen and a nitrogen compound selected from the group consisting of primary and secondary amines in the presence of a heterogeneous catalyst, wherein the reaction is carried out using a suspended catalyst as heterogeneous catalyst and is carried out in the semibatch mode in which the nitrogen compound as one reactant is placed in the reaction vessel and the aldehyde and/or the ketone as the other reactant is added during the course of the reaction and the aldehyde and/or the ketone is added in portions or continuously to the reaction mixture during the course of the reaction as a function of the achieved conversion of the nitrogen compound until a conversion of the nitrogen compound of at least 95% results, and all or part of the catalyst remains in the reaction vessel after the reaction batch and is reused for the next reaction batch.

68 Claims, No Drawings

PROCESS FOR THE PREPARATION OF AN AMINE

CROSS REFERENCE TO RELATED APPLICATIONS

This application is a national phase of PCT/EP2007/055054, filed on May 24, 2007, which claims priority to EP 06114777.3, filed on May 31, 2006, the entire contents of which are incorporated herein by reference in their entireties.

The present invention relates to a process for preparing an amine by reacting an aldehyde and/or ketone with hydrogen and a nitrogen compound selected from the group consisting of primary and secondary amines in the presence of a heterogeneous catalyst.

The process products are used, inter alia, as intermediates in the production of fuel additives (U.S. Pat. No. 3,275,554; DE-A-21 25 039 and DE-A-36 11 230), surfactants, drugs and crop protection agents, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

High-pressure processes, for example, are known for preparing an amine by reacting an aldehyde or ketone with hydrogen and a nitrogen compound. Here, the hydrogenative amination is carried out over a fixed bed of catalyst, using, for example, metal catalysts, comprising Ni, Pd, Pt, promoters on a support.

DE-A-211 82 83 (BASF AG) relates to a process for preparing secondary or tertiary aliphatic or cycloaliphatic amines using a Pd/Ag fixed-bed catalyst. The support material is, in particular, $SiO_2$.

EP-A1-7093 (BASF AG) relates to the preparation of N-aralkyl-2,6-dimethyl-morpholines such as fenpropimorph, over Pd/Ag fixed-bed catalysts.

EP-A1-1 020 424 (BASF AG) relates to the preparation of N-ethyldiisopropylamine over fixed-bed catalysts comprising particular oxidic support materials (e.g. $ZrO_2$).

The European patent application No. 06111505.1 of Mar. 21, 2006 (BASF AG) relates to a process for preparing an amine by reacting an aldehyde and/or ketone with hydrogen and a nitrogen compound in the presence of a heterogeneous catalyst, with the fixed-bed catalyst being a particular coated catalyst.

Low-pressure processes for preparing an amine by hydrogenative amination are also known. Here, noble metal catalysts, for example, are used in suspended form, for example to prepare dimethylcyclohexylamine (DMCHA) over Pd/C: U.S. Pat. No. 4,521,624 (1985) (pressure range: 3.4-40 bar, temperatures: 70 to 135° C.) and CN-A-1 092 061 (1994) (pressure range: 10-50 bar).

JP 10081650 A2, granted as JP 2851274 B2 (Koei Chem.), and JP 02180854 A2, granted as JP 2740828 B2 (Koei Chem.), describe, in particular, the preparation of ethyldiisopropylamine from acetaldehyde and diisopropylamine or from acetone and ethylamine over suspended Pd/C catalysts in the semibatch mode at 20-200° C. and preferably 5-60 atm. These documents teach the removal of the catalyst from the reaction vessel after the reaction is complete and teach nothing about conversion control of the amine used.

EP-A-611 137 (Sumitomo Chem. Comp.) relates to the reductive amination of cyclic ketones, with an appropriate imino compound being prepared in a first stage and subsequently being hydrogenated.

EP-A2-312 253 (Kao Corp.) describes the use of specific copper catalysts in the preparation of n-substituted amines from alcohols or aldehydes.

It was an object of the present invention to overcome one or more disadvantages of the prior art and to find an improved economical process for preparing an amine. In particular, the process should employ a high-activity catalyst which, as a result of skilful choice of the process conditions, displays a high selectivity in the reaction and can be used a number of times. The process product should be obtained in high yields, in particular also space-time yields (STYs).

We have accordingly found a process for preparing an amine by reacting an aldehyde and/or ketone with hydrogen and a nitrogen compound selected from the group consisting of primary and secondary amines in the presence of a heterogeneous catalyst, wherein the reaction
is carried out using a suspended catalyst as heterogeneous catalyst and
is carried out in the semibatch mode in which the nitrogen compound as one reactant is placed in the reaction vessel and the aldehyde and/or the ketone as the other reactant is added during the course of the reaction and the aldehyde and/or the ketone is added in portions or continuously to the reaction mixture during the course of the reaction as a function of the achieved conversion of the nitrogen compound until a conversion of the nitrogen compound of at least 95% results,
and all or part of the catalyst remains in the reaction vessel after the reaction batch and is reused for the next reaction batch.

The advantages of the process of the invention include, inter alia, the fact that in the semibatch mode only low concentrations of unreacted aldehyde/ketone are present during the course of the reaction and only small amounts of by-products, e.g. from the base-catalyzed aldol reaction, are therefore formed. Thanks to the determination of the conversion during the course of the reaction and titered addition of aldehyde/ketone until a high specific minimum conversion is reached, recirculation of unreacted nitrogen component can be dispensed with, especially since the separation of unreacted starting materials, water and any by-products by distillation is often difficult.

The reaction is preferably started up in the following order:
(a) the reactor is charged with the nitrogen compound to be reacted and the catalyst,
(b) the reactor is flushed with nitrogen,
(c) a hydrogen pressure which is lower than the later reaction pressure is set, e.g. a pressure of 10 bar is set when the reaction is to be carried out at a final pressure of 50 bar,
(d) the reactor is heated to the reaction temperature,
(e) the hydrogen pressure is increased to the reaction pressure,
(f) the carbonyl compound is added in portions or continuously to the reaction mixture.

In the process of the invention, the aldehyde and/or the ketone is preferably added to the initially charged nitrogen compound and catalyst at the reaction temperature and reaction pressure.

The addition is carried out, preferably over a period of from 0.5 to 24 hours, more preferably over a period of from 1 to 15 hours, continuously or in portions. The conversion is checked at successive points in time, e.g. every 30 minutes or every 15 minutes, or continuously, e.g. by on-line gas chromatography or on-line spectroscopy. The conversion is, for example, checked by taking a small sample from the reaction and analyzing it to determine its composition, for example by means of gas chromatography. The conversion (Conv) is calculated as the ratio of the amounts of the products formed from the nitrogen compound used to the sum of the amounts of the products formed from the nitrogen compound and unreacted nitrogen compound according to the following formula:

$$Conv = \frac{n_2}{n_2 + n_1} * 100\%$$

where $n_2$=molar amount of products formed from the nitrogen compound and $n_1$=molar amount of unreacted nitrogen compound.

The aldehyde and/or the ketone is fed in until a conversion of at least 95%, preferably at least 96%, particularly preferably at least 97%, e.g. from 97.5 to 99.8%, in each case based on nitrogen compound used, has been achieved.

This means that, depending on the selectivity of the reaction, the aldehyde and/or the ketone is used in an equimolar amount or in excess. The molar starting material ratio of aldehyde and/or ketone to nitrogen compound used is preferably in the range from 1.0 to 3.5, particularly preferably in the range from 1.01 to 1.50, very particularly preferably in the range from 1.02 to 1.25.

In a particularly preferred embodiment of the invention, the addition rate of the aldehyde and/or the ketone is selected so that the respective desired maximum temperature (preferably in the range from 70 to 180° C.) of the reaction is not exceeded. (Rate of addition in, for example, mol of aldehyde and/or ketone per 30 minutes).

The addition of aldehyde or ketone to the nitrogen compound results in reactions in which heat is liberated: the intermediate imine (if the initially charged nitrogen compound is a primary amine) or enamine (if the initially charged nitrogen compound is a secondary amine) is formed in an exothermic reaction with elimination of water. The intermediate is then converted in the presence of hydrogen and the hydrogenation catalyst into the product in a further exothermic reaction (hydrogenation of the double bond). The reaction temperature can be controlled and limited in a very simple manner by slowing or briefly interrupting the addition of the aldehyde and/or ketone before a predetermined maximum temperature is reacted until the reaction mixture has cooled down again by radiation of heat from the reaction vessel or with use of external cooling.

After conclusion of the reaction, the catalyst is allowed to settle in the reaction vessel. Depending on the amine prepared, two phases (an organic phase and an aqueous phase) may be formed in the reaction mixture. The organic phase and preferably, if present, part of the aqueous phase is then discharged from the reactor, preferably via a filter.

It has surprisingly been found that the catalyst retains a very high catalytic activity when all or at least part of it remains in the reaction vessel (reactor) after conclusion of the reaction, preferably, if appropriate, together with the aqueous phase formed or part of the aqueous phase formed in the reaction product mixture. The subsequent reaction batch can then, preferably without further rinsing of the catalyst or other catalyst reactivation (regeneration), be reacted by, according to the invention, once again introducing the nitrogen compound into the reactor, adding hydrogen to the mixture, heating the mixture to the reaction temperature and then adding the aldehyde and/or the ketone. In a particular embodiment of the invention, the nitrogen compound is introduced into the reactor for the subsequent reaction batch by rinsing the abovementioned filter with the same nitrogen compound, so that any catalyst particles present in the filter are again transferred to the reactor.

As a result of part of the aqueous phase remaining in the reaction vessel, the water content in the reaction mixture of the subsequent reaction batch is increased. It has surprisingly been found that the presence of the larger amount of water does not overall have a disadvantageous effect on the reaction, although the preceding equilibrium reaction (formation of the enamine or imine with elimination of water) is adversely affected by the increased water concentration. The advantage of the catalysts retaining a high activity outweighs the disadvantage of the increased hydrogen concentration, so that the procedure described for the recirculation of catalyst is advantageous overall.

"Part of the catalyst remaining in the reaction vessel" means, in particular, that at least 30% by weight, preferably at least 50% by weight, more preferably at least 70% by weight, very particularly preferably at least 90% by weight, of the catalyst originally used remains in the reaction vessel after the reaction has been carried out and the organic reaction products have been separated off.

"Part of the aqueous phase remaining in the reaction vessel" means, in particular, that at least 20% by weight, preferably at least 30% by weight, more preferably at least 40% by weight, very particularly preferably at least 50% by weight, of the aqueous phase formed after the reaction has been carried out remain in the reaction vessel.

A further advantage of the process of the invention is thus very simple and rapid progression from batch to batch without complicated catalyst discharge in which amounts of catalyst can come into contact with air or remain on the filter (losses of material). Without the complicated catalyst handling, the process can be operated more reliably and at the same time the production costs are reduced as a result of the catalyst consumption being minimized and the process being able to be carried out quickly (increased capacity in existing plants) and with lower working costs (reduced labor requirement).

The process of the invention likewise makes it possible to carry out the reaction with a constant catalyst activity by, for example in the case of a decreasing reaction rate/increased batch times, adding, for example, small amounts of fresh catalyst, which makes an absolutely constant product quality over time possible. The work-up and purification of the crude product is substantially simplified as a result. During a campaign, a largely identical crude product mixture is worked up in all batches. The proportions of desired product (process product) and/or by-products are largely constant. The separation task in the subsequent work-up, e.g. distillation, does not change or changes only insignificantly over time.

In the suspended catalyst of the process of the invention, the catalytically active metals or the metals in their compounds are preferably selected from among the elements of groups 8 and/or 9 and/or 10 and/or 11 of the Periodic Table of the Elements (IUPAC notation 1985).

The process of the invention is preferably carried out in the presence of an unsupported transition metal catalyst as suspended catalyst. Transition metal catalysts which are preferred for the purposes of the invention are, in particular, those which comprise one or more metals selected from the group consisting of the metals Pd, Pt, Ag, Ru, Rh, Ni and Pd as active components. Particular preference is given to Pd as at least one, in particular only, active component. (Active component=catalytically active component).

Possible support materials in the catalysts used according to the invention are, for example, activated carbon, aluminum oxide, silica gel, $CaCO_3$, $BaSO_4$, $ZrO_2$, $TiO_2$, preferably activated carbon and aluminum oxide and particularly preferably activated carbon.

A catalyst which is particularly preferred for the purposes of the present invention is Pd on activated carbon (Pd/C).

The catalysts mentioned advantageously have metal contents, in particular noble metal contents, of from 0.1 to 25% by weight, preferably from 0.5 to 15% by weight and particularly preferably from 4 to 11% by weight (in each case based on the reduced metal or reduced metals of the finished catalyst and based on the total mass of the dry catalyst).

Such catalysts are commercially available and can be obtained, for example under the names Degussa E1002, Degussa E101, Degussa E105, Degussa E106, Engelhard C3630, Heraeus K201, Heraeus K202, Heraeus K203, Heraeus K204, Heraeus K219.

The catalyst selected is advantageously used in such an amount that the ratio of the amount of catalyst (calculated on a water-free basis) to the amount of primary or secondary amine to be reacted is in the range from 0.1 to 20.0% by weight, preferably in the range from 0.5 to 5.0% by weight.

The suspended catalyst preferably has a water content in the range from 1 to 70% by weight, more preferably in the range from 30 to 60% by weight.

In a preferred embodiment, the reaction in the process of the invention is carried out without addition of promoters in the catalyst, e.g. additions of zinc, or auxiliaries, e.g. carbon monoxide.

The process of the invention enables aldehydes and ketones to be converted into the corresponding secondary and tertiary amines with high selectivity and in high yield.

The amination of the aldehyde and/or ketone is preferably carried out in the liquid phase.

In an embodiment of the invention, the reaction is carried out in the liquid phase or in a mixed liquid/gas phase with at least 50% by weight of the reaction mixture in the liquid phase.

As reactors, it is possible to use, for example, stirred vessels, autoclaves, loop reactors or packed bubble columns. The preferred reactor is a stirred vessel.

To ensure the formation of a liquid phase, suitable temperature and pressure parameters have to be chosen within the abovementioned ranges, which is dependent on the particular mixture of substances used.

The process of the invention is preferably carried out at an absolute pressure (=reaction pressure) in the range from 1 to 120 bar, preferably from 5 to 100 bar, particularly preferably from 10 to 80 bar. The pressure in the reactor, which is given by the sum of the partial pressures of the aminating agent, the aldehyde and/or ketone component and the reaction products formed at the indicated temperatures, is advantageously increased to the desired reaction pressure by injection of hydrogen.

The inventive process for amination of aldehydes and/or ketones is preferably carried out at a temperature in the range from 15 to 180° C., preferably from 30 to 170° C., particularly preferably from 70 to 160° C.

The process of the invention is preferably carried out with an amount of offgas of from 0.1 to 400 standard cubic meters/h/(liters of reaction volume), in particular from 1 to 20 standard cubic meters/h/(liters of reaction volume).

The use of higher temperatures, higher total pressure and smaller amounts of catalyst is possible.

After the reaction product mixture has advantageously been depressurized, the excess hydrogen and any aminating agent still present in traces are removed from the mixture and the crude reaction product obtained is purified, e.g. by fractional rectification. Suitable work-up methods are described in, for example, EP-A-1 312 600 and EP-A-1 312 599 (both BASF AG).

The process of the invention makes it possible to prepare, for example, amines of the formula I

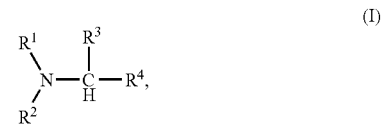

where
$R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxy-alkyl, dialkylaminoalkyl such as $C_{3-30}$-dialkylaminoalkyl, aryl, aralkyl such as $C_{7-20}$-aralkyl or alkylaryl such as $C_{7-20}$-alkylaryl or together are —$(CH_2)_j$—X—$(CH_2)_k$—, ($R^1$ and $R^2$ are not both simultaneously H),
$R^3$, $R^4$ are each hydrogen (H), alkyl such as $C_{1-20}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkyl-aminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, $R^5$—$(OCR^6R^7CR^8R^9)_n$—$(OCR^6R^7)$, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl or Y—$(CH_2)_m$—$NR^5$—$(CH_2)_q$ or together are —$(CH_2)_l$—X—$(CH_2)_m$— or
$R^2$ and $R^4$ together are —$(CH_2)_l$—X—$(CH_2)_m$—,
$R^5$, $R^{10}$ are each hydrogen (H), alkyl such as $C_{1-4}$-alkyl, alkylphenyl such as $C_{7-40}$-alkylphenyl,
$R^6$, $R^7$, $R^8$, $R^9$ are each hydrogen (H), methyl or ethyl,
X is $CH_2$, $CHR^5$, oxygen (O), sulfur (S) or $NR^5$,
Y is $N(R^{10})_2$, hydroxy, $C_{2-20}$-alkylaminoalkyl or $C_{3-20}$-dialkylaminoalkyl,
n is an integer from 1 to 30 and
j, k, l, m, q are each an integer from 1 to 4.

The process of the invention is therefore preferably employed for preparing an amine I in which an aldehyde and/or a ketone of the formula VI or VII

is reacted with a nitrogen compound of the formula III

where $R^1$, $R^2$, $R^3$ and $R^4$ are as defined above.

As can be seen from the definitions of the radicals. $R^2$ and $R^4$, the reaction can also occur intramolecularly in an appropriate amino ketone or amino aldehyde.

To prepare the amine I, a hydrogen atom of the nitrogen compound III is accordingly replaced purely formally by the radical $R^4(R^3)CH$— with liberation of one molar equivalent of water.

The substituents $R^1$ to $R^{10}$, the variables X, Y and the indices j, k, l, m, n and q in the compounds I, III, VI and VII independently have the following meanings:

$R^1$, $R^2$, $R^3$, $R^4$, $R^5$, $R^6$, $R^7$, $R^8$, $R^9$, $R^{10}$:
  hydrogen (H), ($R^1$ and $R^2$ are not both simultaneously H), $R^3$, $R^4$:
  alkyl such as $C_{1-20}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl,
  hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl)-ethyl,
  aminoalkyl such as $C_{1-20}$-aminoalkyl, preferably $C_{1-8}$-aminoalkyl such as amino-methyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl,
  hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxyethylamino)ethyl and 3-(2-hydroxyethylamino)propyl,
  $R^5$—$(OCR^6R^7CR^8R^9)_n$—$(OCR^6R^7)$, preferably $R^5$—$(OCHR^7CHR^9)_n$—$(OCR^6R^7)$, particularly preferably $R^5$—$(OCH_2CHR^9)_n$—$(OCR^6R^7)$,
  alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-methylamino-ethyl, ethylaminomethyl, 2-ethylaminoethyl and 2-(isopropylamino)ethyl, $(R^5)HN$—$(CH_2)_q$, Y—$(CH_2)_m$—$NR^5$—$(CH_2)_q$,
  heteroarylalkyl such as $C_{4-20}$-heteroarylalkyl such as pyrid-2-ylmethyl, furan-2-ylmethyl, pyrrol-3-ylmethyl and imidazol-2-yl-methyl,
  alkylheteroaryl such as $C_{4-20}$-alkylheteroaryl such as 2-methyl-3-pyridinyl, 4,5-dimethylimidazol-2-yl, 3-methyl-2-furanyl and 5-methyl-2-pyrazinyl,
  heteroaryl such as 2-pyridinyl, 3-pyridinyl, 4-pyridinyl, pyrazinyl, pyrrol-3-yl, imidazol-2-yl, 2-furanyl and 3-furanyl, $R^1$, $R^2$, $R^3$, $R^4$:
  cycloalkyl such as $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl and cyclohexyl,
  alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly $C_{2-4}$-alkoxyalkyl,
  dialkylaminoalkyl such as $C_{3-30}$-dialkylaminoalkyl, preferably $C_{3-20}$-dialkyl-aminoalkyl, particularly preferably $C_{3-10}$-dialkylaminoalkyl such as N,N-dimethyl-aminomethyl, (N,N-dibutylamino)methyl, 2-(N,N-dimethylamino)ethyl, 2-(N,N-diethyl-amino)ethyl, 2-(N,N-dibutylamino)ethyl, 2-(N,N-di-n-propylamino)ethyl and 2-(N,N-diisopropylamino)ethyl, 3-(N,N-dimethylamino)propyl, $(R^5)_2N$—$(CH_2)_q$,
  aryl such as phenyl, 1-naphthyl, 2-naphthyl, 1-anthryl, 2-anthryl and 9-anthryl, preferably phenyl, 1-naphthyl and 2-naphthyl, particularly preferably phenyl,
  alkylaryl such as $C_{7-20}$-alkylaryl, preferably $C_{7-12}$-alkylphenyl such as 2-methyl-phenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl,
  aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl,
  $R^3$ and $R^4$ or $R^2$ and $R^4$ together are a —$(CH_2)_l$—X—$(CH_2)_m$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^1$, $R^2$:
  alkyl such as $C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, particularly preferably $C_{1-4}$-alkyl, or
  $R^1$ and $R^2$ together are a—$(CH_2)_l$—X—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^5$, $R^{10}$:
  alkyl, preferably $C_{1-4}$-alkyl such as methyl, ethyl, n-propyl, isopropyl, n-butyl, isobutyl, sec-butyl and tert-butyl, preferably methyl and ethyl, particularly preferably methyl, alkylphenyl, preferably $C_{7-40}$-alkylphenyl such as 2-methylphenyl, 3-methylphenyl, 4-methylphenyl, 2,4-diethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, preferably $C_{7-20}$-alkylphenyl, $R^6, R^7, R^8, R^9$:
methyl or ethyl, preferably methyl, X:
$CH_2$, $CHR^5$, oxygen (O), sulfur (S) or $NR^5$, preferably $CH_2$ and O, Y:
$N(R^{10})_2$, preferably $NH_2$ and $N(CH_3)_2$,
hydroxy (OH),
$C_{2-20}$-alkylaminoalkyl, preferably $C_{2-16}$-alkylaminoalkyl such as methylamino-methyl, 2-methylaminoethyl, ethylaminomethyl, 2-ethylaminoethyl and 2-(isopropylamino)ethyl,
$C_{3-20}$-dialkylaminoalkyl, preferably $C_{3-16}$-dialkylaminoalkyl such as dimethylamino-methyl, 2-dimethylaminoethyl, 2-diethylaminoethyl, 2-(di-n-propylamino)ethyl and 2-(diisopropylamino)ethyl, j, l:
an integer from 1 to 4 (1, 2, 3 or 4), preferably 2 and 3, particularly preferably 2, k, m, q:
an integer from 1 to 4 (1, 2, 3 or 4), preferably 2, 3 and 4, particularly preferably 2 and 3, n:
an integer from 1 to 30, preferably an integer from 1 to 8 (1, 2, 3, 4, 5, 6, 7 or 8), particularly preferably an integer from 1 to 6.

Ketones which can be used in the process of the invention are, subject to the abovementioned preconditions, virtually all aliphatic and aromatic ketones. The aliphatic ketones can be straight-chain, branched or cyclic and the ketones can comprise heteroatoms. The ketones can also bear substituents or comprise functional groups which are inert under the conditions of the hydrogenative amination, for example alkoxy, alkenyloxy, alkylamino or dialkylamino groups, or may be hydrogenated under the conditions of the hydrogenative amination, for example C—C double or triple bonds. If a plurality of ketones are to be aminated, it is possible to obtain amino ketones, amino alcohols, cyclic amines or multiply aminated products by controlling the reaction conditions.

Preference is given to aminatively hydrogenating, for example, the following ketones:
acetone, ethyl methyl ketone, methyl vinyl ketone, isobutyl methyl ketone, butanone, 3-methylbutan-2-one, diethyl ketone, tetralone, acetophenone, propiophenone, p-methylacetophenone, p-methoxyacetophenone, m-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclo-hexanone, cycloheptanone, cyclododecanone, acetylacetone, methylglyoxal and benzophenone.

Aldehydes which can be used in the process of the invention are, subject to the abovementioned preconditions, virtually all aliphatic and aromatic aldehydes. The aliphatic aldehydes can be straight-chain, branched or cyclic and the aldehydes can comprise heteroatoms. The aldehydes can also bear substituents or comprise functional groups which are inert under the conditions of the hydrogenative amination, for example alkoxy, alkenyloxy, alkylamino or dialkylamino groups, or may be hydrogenated under the conditions of the hydrogenative amination, for example C—C double or triple bonds. If polyfunctional aldehydes or ketoaldehydes are to be aminated, it is possible to obtain amino alcohols, cyclic amines or multiply aminated products by controlling the reaction conditions.

Preference is given to aminatively hydrogenating, for example, the following aldehydes:
formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methyl-pentanal, 4-methylpentanal, glyoxal, benzaldehyde, p-methoxybenzaldehyde, p-methylbenzaldehyde, phenylacetaldehyde, (p-methoxy-phenyl)acetaldehyde, (3,4-dimethoxyphenyl)acetaldehyde, 4-formyltetrahydropyran, 3-formyltetrahydrofuran, 5-formylvaleronitrile, citronellal, lysmeral, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and also hydroformylated oligomers and polymers such as hydroformylated polyisobutene (polyisobutenaldehyde) or the oligomer obtained by metathesis of 1-pentene and cyclopentene and hydroformylation.

As aminating agents in the hydrogenative amination of aldehydes and/or ketones in the presence of hydrogen, it is possible to use primary or secondary, aliphatic or cycloaliphatic or aromatic amines.

Cyclic amines such as pyrrolidines, piperidines, hexamethylenimines, piperazines and morpholines can be prepared from dialdehydes or oligoaldehydes or diketones or oligoketones or ketoaldehydes by intramolecular hydrogenative amination.

The primary or secondary amines are preferably used as aminating agents for preparing unsymmetrically substituted dialkylamines or trialkylamines, e.g. ethyldiisopropylamine and ethyldicyclohexylamine.

For example, the following monoalkylamines and dialkylamines are used as aminating agents: methylamine, dimethylamine, ethylamine, diethylamine, n-propylamine, di-n-propylamine, isopropylamine, diisopropylamine, dimethylmorpholine, isopropyl-ethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, bis(2-ethylhexyl)amine, cyclohexylamine, aniline, toluidine, piperidine, morpholine and pyrrolidine.

Amines which are particularly preferably prepared by the process of the invention are, for example, N,N-di($C_{1-4}$-alkyl)cyclohexylamine (from cyclohexanone and di($C_{1-4}$-alkyl)-amine), dicyclohexylamine (from cyclohexanone and cyclohexylamine), N,N-dimethyl-N-propylamine (from n-propanal and dimethylamine), N,N-dimethyl-N-isopropylamine (from acetone and DMA), N-ethyl-N,N-diisopropylamine (from acetaldehyde and N,N-diisopropylamine), tris(2-ethylhexyl)amine (from 2-ethylhexanal and bis(2- ethylhexyl)amine), and cis-4-[3-(4-tert-butylphenyl)-2-methylpropyl]-2,6-dimethyl-morpholine (from lysmeral and cis-2,6-dimethylmorpholine).

Very particularly preferred processes according to the invention are those a) for preparing N-ethyl-N,N-diisopropylamine (Hünig base) by reacting acetaldehyde with diisopropylamine, preferably using a suspended Pd/C catalyst, with the reaction preferably being carried out at an absolute pressure in the range from 20 to 100 bar, particularly preferably from 25 to 80 bar, more particularly preferably from 40 to 75 bar, and preferably at a temperature in the range from 70 to 170° C., particularly preferably from 80 to 140° C., more particularly preferably from 90 to 120° C., and b) for preparing tris(2-ethylhexyl)amine by reacting 2-ethylhexanal with bis(2-ethylhexyl)amine, preferably using a suspended Pd/C catalyst, with the reaction preferably being carried out at an absolute pressure in the range from 20 to 100 bar, particularly preferably from 25 to 80 bar, more particularly preferably from 40 to 75 bar, and preferably at a temperature in the range from 100 to 170° C., particularly preferably from 120 to 160° C.

All ppm figures in this document are by weight.

EXAMPLES

Laboratory Experiments on the Synthesis of N-ethyl-N,N-diisopropylamine (EDIPA)

The laboratory experiments were carried out in a 500 ml stirring autoclave from Büchi. Diisopropylamine (DIPA) was placed in the autoclave in which the respective suspended catalyst had been installed. The reactor was flushed with nitrogen. The reactor was pressurized with a low hydrogen pressure and the mixture was heated to the reaction temperature. After the reaction temperature had been reached, the hydrogen pressure was increased to the desired reaction pressure. The acetaldehyde was added during the course of the experiment by means of a pump at the reaction pressure over a period of from 1 to 5 hours (semibatch mode). Samples were taken from the reactor at regular intervals and analyzed by gas chromatography. The aldehyde was added in such an amount that a DIPA conversion of at least 95% was achieved, which resulted in a molar aldehyde excess of 20%. The stirrer speed was from 300 to 1200 rpm. The reaction temperature was 100° C. and the reaction pressure was 25 bar. Catalysts used were carbon-supported, palladium-comprising suspended catalysts comprising 5% of Pd on carbon (water content: about 50%). A specific amount of catalyst of 0.03 g (catalyst calculated as 100%)/g (diisopropylamine) was used, i.e. as 6% by weight of water-moist catalyst, based on DIPA.

The reaction product mixtures were analyzed by means of gas chromatography. The measurement program used was: separation column DB1, length: 60 m; internal diameter: 0.32 mm; carrier gas: helium; temperature program: 80° C., then at 5° C./minute to 260° C., finally 10 minutes isothermal at 260° C.

Table 1 shows the results of the various experiments (composition of the organic phase in GC-% by area). Multiple catalyst recirculation was carried out successfully without an appreciable decrease in the catalyst activity (entries 4 to 6 in Table 1).

TABLE 1

Laboratory experiments on the synthesis of EDIPA

| No. | Addition time h | Reaction time h | Ethanol % | DIPA % | EDIPA % | Diisopropyl-butylamine % | Diisopropyl-butanolamine % | Others % |
| --- | --- | --- | --- | --- | --- | --- | --- | --- |
| 1 | 1 | 4 | 1.7 | 0.4 | 94.9 | 1.1 | 1.1 | 1.9 |
| 2 | 3 | 6 | 1.2 | 1.1 | 94.6 | 1.3 | 1.0 | 1.8 |
| 3 | 5 | 8 | 1.2 | 0.7 | 93.4 | 1.8 | 1.5 | 2.9 |
| 4 | 3 | 6 | 1.4 | 1.5 | 95.2 | 0.9 | 0.5 | 1.0 |
| 5* | 3 | 6 | 0.9 | 0.1 | 95.1 | 1.5 | 0.8 | 2.4 |
| 6* | 3 | 6 | 0.7 | 0.1 | 95.0 | 1.7 | 0.9 | 2.6 |

*Recirculation of catalyst from Experiment No. 4

Industrial Synthesis of N-ethyl-N,N-diisopropylamine

The experiment was carried out in a stirring autoclave. From 2170 to 4100 kg of diisopropylamine (DIPA) were placed in the reactor in which 140 kg of the carbon-supported, palladium-comprising suspended catalyst comprising 5% of Pd on carbon (water content: about 50%) had been installed. The reactor was flushed with nitrogen. A low hydrogen pressure was set and the mixture was subsequently heated to the reaction temperature. As soon as the reaction temperature had been reached, the hydrogen pressure was increased to the desired reaction pressure. The acetaldehyde (from 1130 to 2233 kg) was added at a metering rate of from 120 to 300 kg/h during the course of the experiment. The DIPA conversion was determined during the course of the experiment and the aldehyde was added in such an amount that a conversion of at least 95% was achieved. This resulted in molar aldehyde excesses of from 20 to 64%.

Table 2 shows the results of the 13 reaction batches (reaction parameters and composition of the organic phase in GC-% by area). Recirculation of the catalyst was successfully carried out 12 times without an appreciable decrease in the catalyst activity.

TABLE 2

Production experiment on the synthesis of EDIPA; reaction parameters and composition of the organic phase of the reaction product mixture

| No. | Temperature °C. | Pressure bar | Ethanol % | DIPA % | EDIPA % | Diisopropyl-butylamine % | Diisopropyl-butanol-amine % | Others % |
|---|---|---|---|---|---|---|---|---|
| 1 | 100 | 25 | 8.0 | 2.1 | 81.8 | 3.2 | 0.9 | 4.0 |
| 2 | 100 | 25 | 1.3 | 2.8 | 85.3 | 6.3 | 1.3 | 3.0 |
| 3 | 100 | 50 | 0.8 | 1.9 | 86.0 | 6.7 | 1.1 | 3.5 |
| 4 | 100 | 25 | 0.7 | 1.2 | 81.6 | 11.0 | 1.5 | 4.1 |
| 5 | 120 | 25 | 0.7 | 1.7 | 86.9 | 7.3 | 0.7 | 2.8 |
| 6 | 100 | 25 | 0.5 | 2.6 | 83.4 | 9.6 | 1.0 | 2.9 |
| 7 | 120 | 50 | 0.9 | 1.9 | 88.1 | 6.3 | 0.6 | 2.2 |
| 8 | 120 | 50 | 1.4 | 2.0 | 85.2 | 7.6 | 0.5 | 3.4 |
| 9 | 120 | 50 | 1.2 | 2.9 | 86.4 | 6.7 | 0.5 | 2.4 |
| 10 | 120 | 50 | 1.4 | 2.5 | 82.3 | 9.8 | 0.5 | 3.6 |
| 11 | 130 | 50 | 1.7 | 2.9 | 86.5 | 6.3 | 0.3 | 2.5 |
| 12 | 130 | 50 | 1.8 | 2.0 | 84.7 | 7.9 | 0.3 | 3.4 |
| 13 | 130 | 50 | 1.6 | 3.0 | 84.6 | 7.9 | 0.3 | 2.5 |

Industrial Synthesis of tris(2-ethylhexyl)amine(tris-EH)

The experiment was carried out in a stirring autoclave. 4000 kg of bis(2-ethylhexylamine (di-EH) was placed in the reactor in which from 40 to 150 kg of the carbon-supported, palladium-comprising suspended catalyst comprising 5% of Pd on carbon (water content: about 50%) had been installed. The reactor was flushed with nitrogen. A low hydrogen pressure was set and the mixture was subsequently heated to the reaction temperature. As soon as the reaction temperature had been reached, the hydrogen pressure was increased to the desired reaction pressure. The aldehyde 2-ethylhexanal (2-EH, from 2120 to 2320 kg) was subsequently added continuously. The di-EH conversion was determined during the course of the experiment and the aldehyde was added in such an amount that a conversion of at least 95% was achieved. This resulted in molar aldehyde excesses of from 0.1 to 9%. The predominant by-product formed was small amounts of ethylhexanol (E-ol). Table 3 shows the results of the 33 reaction batches (reaction parameters and composition of the organic phase in GC-% by area). After the 1st, 3rd, 8th and 15th batches, fresh catalyst was introduced into the reactor, as a result of which the amount of catalyst increased to a final value of 150 kg. From batch 16, the catalyst was recirculated 17 times without an appreciable decrease in the catalyst activity.

TABLE 3

Production experiment on tris(2-ethylhexyl)amine; reaction parameters and composition of the organic phase of the reaction product mixture

| No. | Temperature °C. | Pressure bar | Reaction time h | Tris-EH % | Di-EH % | 2-EH % | E-ol % | Amount of catalyst kg | Addition of 2-EH kg |
|---|---|---|---|---|---|---|---|---|---|
| 1 | 80 | 50 | 52 | 86.2 | 2.9 | 0.8 | 8.7 | 40 | 2120 |
| 2 | 123 | 50 | 35 | 92.1 | 1.7 | 0.2 | 4.9 | 60 | 2320 |
| 3 | 127 | 50 | 31 | 92.8 | 2.0 | 0.4 | 5.9 | 60 | 2320 |
| 4 | 127 | 50 | 17 | 94.1 | 1.3 | 0.5 | 4.4 | 80 | 2120 |
| 5 | 135 | 50 | 23 | 93.7 | 0.5 | 3.9 | 0.6 | 80 | 2320 |
| 6 | 135 | 60 | 13 | 88.6 | 3.0 | 3.5 | 3.6 | 80 | 2120 |
| 7 | 135 | 60 | 19 | 89.6 | 3.5 | 0.8 | 4.9 | 80 | 2120 |
| 8 | 135 | 60 | 12 | 91.0 | 3.3 | 1.5 | 2.5 | 100 | 2120 |
| 9 | 135 | 60 | 10 | 91.4 | 2.3 | 1.9 | 3.5 | 100 | 2326 |
| 10 | 135 | 40 | 12 | 93.7 | 1.0 | 1.6 | 2.8 | 100 | 2320 |
| 11 | 135 | 40 | 13 | 93.5 | 2.3 | 1.3 | 1.8 | 100 | 2222 |
| 12 | 135 | 40 | 10 | 92.2 | 3.2 | 2.0 | 1.6 | 100 | 2222 |
| 13 | 135 | 40 | 11 | 92.3 | 3.1 | 1.8 | 1.8 | 100 | 2222 |
| 14 | 135 | 40 | 9 | 91.7 | 3.3 | 2.4 | 1.6 | 100 | 2222 |
| 15 | 135 | 40 | 5 | 93.3 | 1.5 | 2.5 | 1.6 | 150 | 2307 |
| 16 | 135 | 40 | 5 | 93.6 | 2.0 | 2.0 | 1.3 | 150 | 2228 |
| 17 | 135 | 30 | 6 | 94.3 | 1.7 | 1.8 | 1.1 | 150 | 2225 |
| 18 | 135 | 20 | 9 | 95.7 | 1.4 | 2.2 | 0.9 | 150 | 2223 |
| 19 | 140 | 20 | 6 | 91.4 | 3.7 | 2.6 | 0.8 | 150 | 2224 |
| 20 | 140 | 40 | 5 | 92.7 | 2.6 | 2.4 | 1.2 | 150 | 2221 |
| 21 | 140 | 40 | 7 | 94.4 | 1.0 | 1.1 | 2.2 | 150 | 2253 |
| 22 | 140 | 40 | 5 | 89.6 | 4.6 | 2.2 | 2.5 | 150 | 2220 |
| 23 | 140 | 40 | 7 | 94.5 | 1.9 | 1.6 | 1.1 | 150 | 2224 |
| 24 | 140 | 40 | 6 | 93.5 | 2.1 | 2.3 | 1.1 | 150 | 2238 |
| 25 | 140 | 40 | 5 | 93.2 | 2.1 | 1.3 | 1.3 | 150 | 2222 |
| 26 | 140 | 40 | 6 | 94.2 | 2.2 | 1.2 | 1.1 | 150 | 2233 |
| 27 | 140 | 40 | 6 | 92.6 | 3.2 | 1.7 | 1.0 | 150 | 2223 |
| 28 | 140 | 40 | 14 | 96.0 | 0.2 | 0.4 | 2.0 | 150 | 2226 |
| 29 | 150 | 60 | 13 | 95.6 | 0.8 | 0.0 | 2.7 | 150 | 2236 |
| 30 | 150 | 60 | 9 | 94.5 | 2.7 | 0.0 | 1.6 | 150 | 2222 |

TABLE 3-continued

Production experiment on tris(2-ethylhexyl)amine; reaction parameters and composition of the organic phase of the reaction product mixture

| No. | Temperature °C. | Pressure bar | Reaction time h | Tris-EH % | Di-EH % | 2-EH % | E-ol % | Amount of catalyst kg | Addition of 2-EH kg |
|---|---|---|---|---|---|---|---|---|---|
| 31 | 150 | 60 | 11 | 93.0 | 2.0 | 0.0 | 3.6 | 150 | 2222 |
| 32 | 155 | 60 | 14 | 95.8 | 0.8 | 0.1 | 2.3 | 150 | 2222 |
| 33 | 155 | 60 | 13 | 95.4 | 1.4 | 0.1 | 1.8 | 150 | 2236 |

The invention claimed is:

1. A process for preparing N-ethyl-N,N-diisopropyl-amine (Hünig base) by reacting acetaldehyde with hydrogen and diisopropylamine in the presence of a heterogeneous catalyst, wherein the reaction is carried out using a suspended catalyst as heterogeneous catalyst and is carried out in the semibatch mode in which the diisopropylamine as one reactant is placed in the reaction vessel and the acetaldehyde as the other reactant is added during the course of the reaction and the acetaldehyde is added in portions or continuously to the reaction mixture during the course of the reaction as a function of the achieved conversion of the diisopropylamine until a conversion of the diisopropylamine of at least 95% results, and all or part of the catalyst remains in the reaction vessel after the reaction batch and is reused for the next reaction batch.

2. The process according to claim 1, wherein the reaction is carried out using a suspended Pd/C catalyst.

3. The process according to claim 1, wherein the reaction is carried out at an absolute pressure in the range from 20 to 100 bar and a temperature in the range from 70 to 170° C.

4. A process for preparing tris(2-ethylhexyl)amine by reacting 2-ethylhexanal with hydrogen and bis(2-ethylhexyl)amine in the presence of a heterogeneous catalyst, wherein the reaction is carried out using a suspended catalyst as heterogeneous catalyst and is carried out in the semibatch mode in which the bis(2-ethylhexyl)amine as one reactant is placed in the reaction vessel and the 2-ethylhexanal as the other reactant is added during the course of the reaction and the 2-ethylhexanal is added in portions or continuously to the reaction mixture during the course of the reaction as a function of the achieved conversion of the bis(2-ethylhexyl)amine until a conversion of the bis(2-ethylhexyl)amine of at least 95% results, and all or part of the catalyst remains in the reaction vessel after the reaction batch and is reused for the next reaction batch.

5. The process according to claim 4, wherein the reaction is carried out using a suspended Pd/C catalyst.

6. The process according to claim 4, wherein the reaction is carried out at an absolute pressure in the range from 20 to 100 bar and a temperature in the range from 100 to 170° C.

7. A process for preparing cis-4- [3-(4-tert-butylphenyl)-2-methylpropyl]2,6-dimethylmorpholine by reacting lysmeral with hydrogen and cis-2,6-dimethylmorpholine in the presence of a heterogeneous catalyst, wherein the reaction is carried out using a suspended catalyst as heterogeneous catalyst and is carried out in the semibatch mode in which the cis-2,6-dimethylmorpholine as one reactant is placed in the reaction vessel and the lysmeral as the other reactant is added during the course of the reaction and the lysmeral is added in portions or continuously to the reaction mixture during the course of the reaction as a function of the achieved conversion of the cis-2,6-dimethylmorpholine until a conversion of the cis-2,6-dimethylmorpholine of at least 95% results, and all or part of the catalyst remains in the reaction vessel after the reaction batch and is reused for the next reaction batch.

8. A process for preparing N,N-dimethyl-cyclohexylamine by reacting cyclohexanone with hydrogen and dimethylamine in the presence of a heterogeneous catalyst, wherein the reaction is carried out using a suspended catalyst as heterogeneous catalyst and is carried out in the semibatch mode in which the dimethylamine as one reactant is placed in the reaction vessel and the cyclohexanone as the other reactant is added during the course of the reaction and the cyclohexanone is added in portions or continuously to the reaction mixture during the course of the reaction as a function of the achieved conversion of the dimethylamine until a conversion of the dimethylamine of at least 95% results, and all or part of the catalyst remains in the reaction vessel after the reaction batch and is reused for the next reaction batch.

9. A process for preparing N,N-dimethyl-N-isopropyl-amine by reacting acetone with hydrogen and dimethylamine in the presence of a heterogeneous catalyst, wherein the reaction is carried out using a suspended catalyst as heterogeneous catalyst and is carried out in the semibatch mode in which the dimethylamine as one reactant is placed in the reaction vessel and the acetone as the other reactant is added during the course of the reaction and the the acetone is added in portions or continuously to the reaction mixture during the course of the reaction as a function of the achieved conversion of the dimethylamine until a conversion of the dimethylaine of at least 95% results, and all or part of the catalyst remains in the reaction vessel after the reaction batch and is reused for the next reaction batch.

10. A process for preparing preparing dicyclohexylamine by reacting cyclohexanone with hydrogen and cyclohexylamine in the presence of a heterogeneous catalyst, wherein the reaction is carried out in the semibatch mode in which the cyclohexylamine as one reactant is placed in the reaction vessel and the cyclohexanone as the other reactant is added during the course of the reaction and the cyclohexanone is added in portions continuously to the reaction mixture during the course of the reaction as a function of the achieved conversion of the cyclohexylamine until a conversion of the cyclohexylamine of at least 95% results, and all or part of the catalyst remains in the reaction vessel after the reaction batch and is reused for the next reaction batch.

11. A process for preparing N,N-dimethyl-N-n-propylamine by reacting propanal with hydrogen and dimethylamine in the presence of a heterogeneous catalyst, wherein the reaction is carried out in the semibatch mode in which the dimethylamine as one reactant is placed in the reaction vessel and the propanal as the other reactant is added during the course of the reaction and the propanal is added in portions continuously to the reaction mixture during the course of the reaction as a function of the achieved conversion of the dimethylamine until a conversion of the dimethylamine of at least 95% results, and all or part of the catalyst remains in the reaction vessel after the reaction batch and is reused for the next reaction batch.

12. The process according to claim 1, wherein all or part of the catalyst remains in the reaction vessel together with the aqueous phase formed or part of the aqueous phase formed after the reaction batch and is reused.

13. The process according to claim 1, wherein all or part of the catalyst remains in the reaction vessel after the reaction batch and is reused without rinsing or regeneration.

14. The process according to claim 1, wherein the acetaldehyde is added in portions or continuously to the reaction mixture during the course of the reaction as a function of the achieved conversion of the diisopropylamine until a conversion of the diisopropylamine of at least 96% results.

15. The process according to claim 1, wherein the reaction is carried out at a temperature in the range from 15 to 180° C.

16. The process according to claim 1, wherein, in the reaction, the diisopropylamine and the catalyst are initially charged and the acetaldehyde is added at a rate which is selected so that the desired maximum temperature of the reaction is not exceeded.

17. The process according to claim 1, wherein the reaction is started up in the following order:
    (a) the reactor is charged with the diisopropylamine and catalyst,
    (b) the reactor is flushed with nitrogen,
    (c) a hydrogen pressure which is lower than the later reaction pressure is set,
    (d) the reactor is heated to the reaction temperature,
    (e) the hydrogen pressure is increased to the reaction pressure,
    (f) the acetaldehyde is added in portions or continuously to the reaction mixture.

18. The process according to claim 1, wherein the reaction is carried out in the liquid phase.

19. The process according to claim 1, wherein the reaction is carried out in the liquid phase or in a mixed liquid/gas phase with at least 50% by weight of the reaction mixture in the liquid phase.

20. The process according to claim 1, wherein the reaction is carried out at an absolute pressure (=reaction pressure) in the range from 1 to 120 bar.

21. The process according to claim 1, wherein the acetaldehyde is used in 1.0- to 3.5-fold molar amount based on the diisopropylamine.

22. The process according to claim 1, wherein the catalytically active metals or the metals in their compounds in the suspended catalyst are selected from among the elements of groups 8 and/or 9 and/or 10 and/or 11 of the Periodic Table of the Elements (IUPAC notation 1985).

23. The process according to claim 1, wherein the suspended catalyst is a supported transition metal catalyst comprising Pd as catalytically active metal.

24. The process according to claim 23, wherein the supported transition metal catalyst comprises activated carbon as support.

25. The process according to claim 23, wherein the supported transition metal catalyst comprises aluminum oxide as support.

26. The process according to claim 1, wherein the suspended catalyst has a noble metal content in the range from 0.1 to 25% by weight (based on the total mass of the catalyst, without water).

27. The process according to claim 1, wherein the suspended catalyst has a noble metal content in the range from 0.5 to 15% by weight (based on the total mass of the catalyst, without water).

28. The process according to claim 1, wherein the suspended catalyst has a water content in the range from 1 to 70% by weight.

29. The process according to claim 1, wherein the catalyst is used in such an amount that the ratio of the amount of catalyst (calculated on a water-free basis) to the amount of diisopropylamine to be reacted is in the range from 0.1 to 20.0% by weight.

30. The process according to claim 1, wherein the reaction is carried out without addition of a promoter or auxiliary.

31. The process according to claim 4, wherein all or part of the catalyst remains in the reaction vessel together with the aqueous phase formed or part of the aqueous phase formed after the reaction batch and is reused.

32. The process according to claim 4, wherein all or part of the catalyst remains in the reaction vessel after the reaction batch and is reused without rinsing or regeneration.

33. The process according to claim 4, wherein the 2-ethylhexanal is added in portions or continuously to the reaction mixture during the course of the reaction as a function of the achieved conversion of the bis(2-ethylhexyl)amine until a conversion of the bis(2-ethylhexyl)amine of at least 96% results.

34. The process according to claim 4, wherein the reaction is carried out at a temperature in the range from 15 to 180° C.

35. The process according to claim 4, wherein, in the reaction, the bis(2-ethylhexyl)amine and the catalyst are initially charged and the 2- ethylhexanal is added at a rate which is selected so that the desired maximum temperature of the reaction is not exceeded.

36. The process according to claim 4, wherein the reaction is started up in the following order:
    (a) the reactor is charged with the bis(2-ethylhexyl)amine and catalyst,
    (b) the reactor is flushed with nitrogen,
    (c) a hydrogen pressure which is lower than the later reaction pressure is set,
    (d) the reactor is heated to the reaction temperature,
    (e) the hydrogen pressure is increased to the reaction pressure,
    (f) the 2-ethylhexanal is added in portions or continuously to the reaction mixture.

37. The process according to claim 4, wherein the reaction is carried out in the liquid phase.

38. The process according to claim 4, wherein the reaction is carried out in the liquid phase or in a mixed liquid/gas phase with at least 50% by weight of the reaction mixture in the liquid phase.

39. The process according to claim 4, wherein the reaction is carried out at an absolute pressure (=reaction pressure) in the range from 1 to 120 bar.

40. The process according to claim 4, wherein the 2-ethylhexanal is used in 1.0- to 3.5-fold molar amount based on the bis(2-ethylhexyl)amine.

41. The process according to claim 4, wherein the catalytically active metals or the metals in their compounds in the suspended catalyst are selected from among the elements of groups 8 and/or 9 and/or 10 and/or 11 of the Periodic Table of the Elements (IUPAC notation 1985).

42. The process according to claim 4, wherein the suspended catalyst is a supported transition metal catalyst comprising Pd as catalytically active metal.

43. The process according to claim 42, wherein the supported transition metal catalyst comprises activated carbon as support.

44. The process according to claim 42, wherein the supported transition metal catalyst comprises aluminum oxide as support.

45. The process according to claim 4, wherein the suspended catalyst has a noble metal content in the range from 0.1 to 25% by weight (based on the total mass of the catalyst, without water).

46. The process according to claim 4, wherein the suspended catalyst has a noble metal content in the range from 0.5 to 15% by weight (based on the total mass of the catalyst, without water).

47. The process according to claim 4, wherein the suspended catalyst has a water content in the range from 1 to 70% by weight.

48. The process according to claim 4, wherein the catalyst is used in such an amount that the ratio of the amount of catalyst (calculated on a water-free basis) to the amount of bis(2-ethylhexyl)amine to be reacted is in the range from 0.1 to 20.0% by weight.

49. The process according to claim 4, wherein the reaction is carried out without addition of a promoter or auxiliary.

50. The process according to claim 7, wherein all or part of the catalyst remains in the reaction vessel together with the aqueous phase formed or part of the aqueous phase formed after the reaction batch and is reused.

51. The process according to claim 7, wherein all or part of the catalyst remains in the reaction vessel after the reaction batch and is reused without rinsing or regeneration.

52. The process according to claim 7, wherein the lysmeral is added in portions or continuously to the reaction mixture during the course of the reaction as a function of the achieved conversion of the cis-2,6-dimethylmorpholine until a conversion of the cis-2,6-dimethylmorpholine of at least 96% results.

53. The process according to claim 7, wherein the reaction is carried out at a temperature in the range from 15 to 180° C.

54. The process according to claim 7, wherein, in the reaction, the cis-2,6-dimethylmorpholine and the catalyst are initially charged and the lysmeral is added at a rate which is selected so that the desired maximum temperature of the reaction is not exceeded.

55. The process according to claim 7, wherein the reaction is started up in the following order:
 (a) the reactor is charged with the cis-2,6-dimethylmorpholine and catalyst,
 (b) the reactor is flushed with nitrogen,
 (c) a hydrogen pressure which is lower than the later reaction pressure is set,
 (d) the reactor is heated to the reaction temperature,
 (e) the hydrogen pressure is increased to the reaction pressure,
 (f) the lysmeral is added in portions or continuously to the reaction mixture.

56. The process according to claim 7, wherein the reaction is carried out in the liquid phase.

57. The process according to claim 7, wherein the reaction is carried out in the liquid phase or in a mixed liquid/gas phase with at least 50% by weight of the reaction mixture in the liquid phase.

58. The process according to claim 7, wherein the reaction is carried out at an absolute pressure (=reaction pressure) in the range from 1 to 120 bar.

59. The process according to claim 7, wherein the lysmeral is used in 1.0- to 3.5-fold molar amount based on the cis-2,6-dimethylmorpholine.

60. The process according to claim 7, wherein the catalytically active metals or the metals in their compounds in the suspended catalyst are selected from among the elements of groups 8 and/or 9 and/or 10 and/or 11 of the Periodic Table of the Elements (IUPAC notation 1985).

61. The process according to claim 7, wherein the suspended catalyst is a supported transition metal catalyst comprising Pd as catalytically active metal.

62. The process according to claim 61, wherein the supported transition metal catalyst comprises activated carbon as support.

63. The process according to claim 61, wherein the supported transition metal catalyst comprises aluminum oxide as support.

64. The process according to claim 7, wherein the suspended catalyst has a noble metal content in the range from 0.1 to 25% by weight (based on the total mass of the catalyst, without water).

65. The process according to claim 7, wherein the suspended catalyst has a noble metal content in the range from 0.5 to 15% by weight (based on the total mass of the catalyst, without water).

66. The process according to claim 7, wherein the suspended catalyst has a water content in the range from 1 to 70% by weight.

67. The process according to claim 7, wherein the catalyst is used in such an amount that the ratio of the amount of catalyst (calculated on a water-free basis) to the amount of cis-2,6-dimethylmorpholine to be reacted is in the range from 0.1 to 20.0% by weight.

68. The process according to claim 7, wherein the reaction is carried out without addition of a promoter or auxiliary.

\* \* \* \* \*